United States Patent [19]

Fiebig, Jr. et al.

[11] 4,411,855
[45] Oct. 25, 1983

[54] METHOD FOR MAKING PERFUME-RELEASE PLASTIC DECORATIONS

[75] Inventors: August E. Fiebig, Jr.; Glenn A. Shurney, both of Chicago; Anton J. Nagy, Crestwood, all of Ill.

[73] Assignee: Alberto-Culver Company, Melrose Park, Ill.

[21] Appl. No.: 296,580

[22] Filed: Aug. 31, 1981

[51] Int. Cl.³ .......................... B29C 5/10; B29C 9/00
[52] U.S. Cl. ................................... 264/219; 264/247; 264/267; 264/319
[58] Field of Search ................. 428/38; 264/80, 259, 264/248, 126, 319, 219, 73, 245–247, 267, 299; 425/4 C, 363; 156/268, 279, 303, 322

[56] References Cited

U.S. PATENT DOCUMENTS

| | | | |
|---|---|---|---|
| 530,817 | 12/1894 | Aumont | 428/81 |
| 1,686,809 | 10/1928 | Grau | 428/38 |
| 2,888,975 | 6/1959 | Benedict | 264/246 |
| 2,987,104 | 6/1961 | Benedict | 156/298 |
| 3,086,245 | 4/1963 | Gits | 264/247 |
| 3,533,889 | 10/1970 | Powell | 428/38 |
| 3,590,107 | 6/1971 | Smith et al. | 264/80 |
| 3,619,456 | 11/1971 | Taylor | 428/38 |
| 3,761,209 | 9/1973 | Hanton | 425/4 C |
| 3,926,655 | 12/1975 | Miles | 106/243 |
| 4,051,159 | 9/1977 | Tsoucalas et al. | 260/18 N |
| 4,067,942 | 1/1978 | Wilson | 264/80 |
| 4,086,738 | 5/1978 | Saccoccio | 264/80 |
| 4,095,031 | 6/1978 | Engle | 526/1 |
| 4,224,275 | 9/1980 | Sauer | 264/259 |

FOREIGN PATENT DOCUMENTS

| | | | |
|---|---|---|---|
| 1418488 | 11/1964 | France | |
| 2083011 | 11/1971 | France | 264/126 |
| 50-20113 | 7/1975 | Japan | 264/247 |
| 52-30024 | 8/1977 | Japan | 264/247 |
| 770610 | 3/1977 | South Africa | |

Primary Examiner—Willard E. Hoag

[57] ABSTRACT

Decorations resembling stained glass miniatures which release perfume into the atmosphere are manufactured from perfume-containing thermoplastic resin compositions and multiple-opening frames. The method of filling the resin composition into the openings of the frames provides a secure interlock between the filled resin and the ribs of the frames, and in a preferred procedure, the bottom surface of the filled resin is clarified to improve the transparency of the filled resin, which is preferably employed in multiple colors.

4 Claims, 19 Drawing Figures

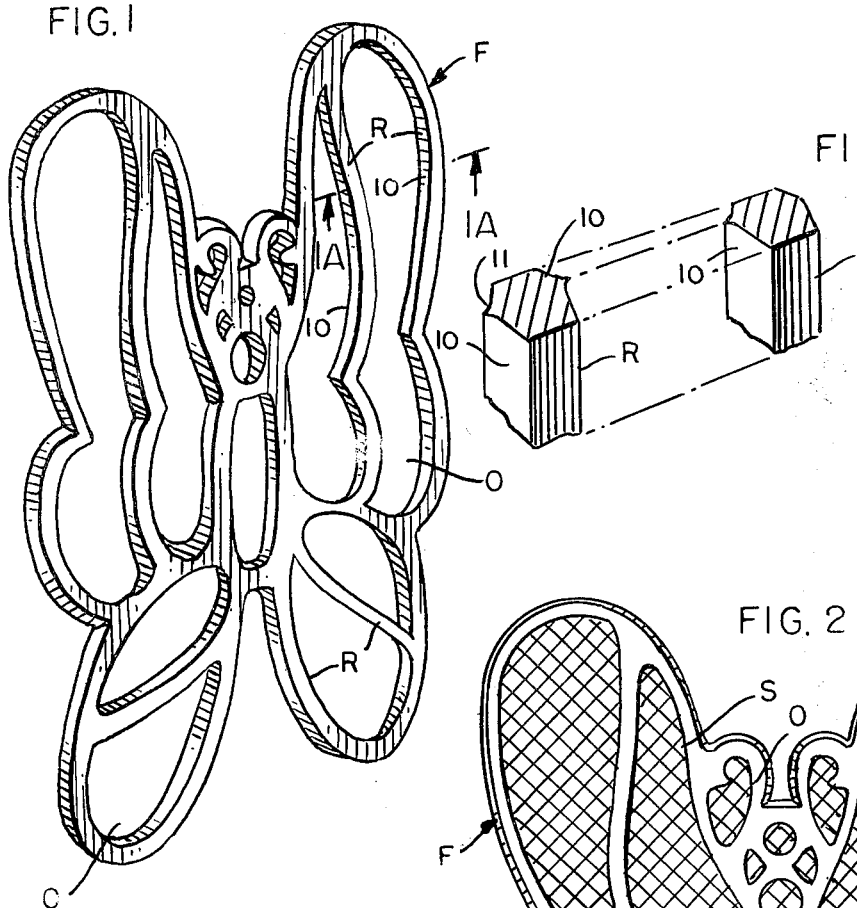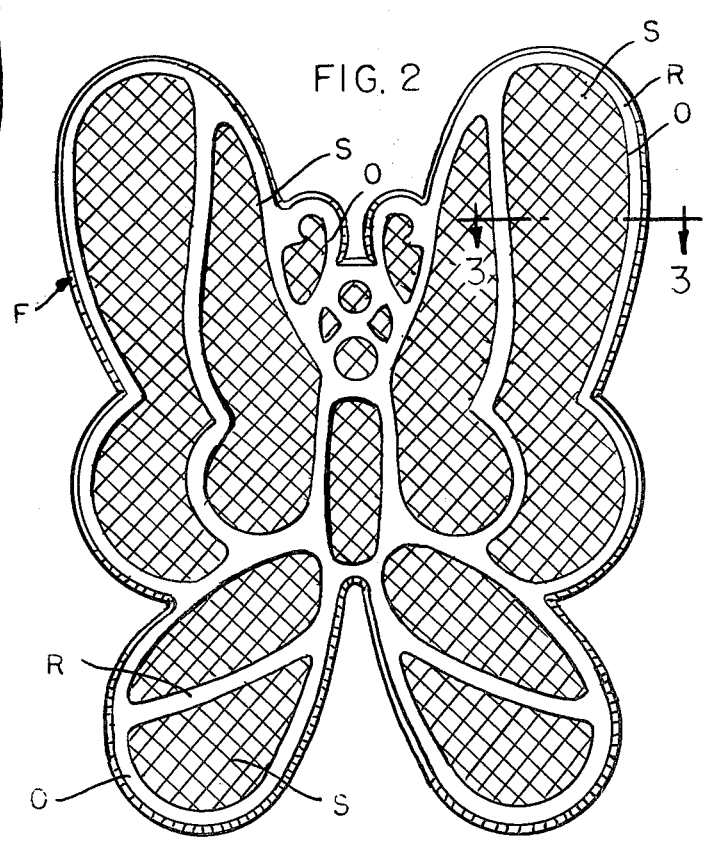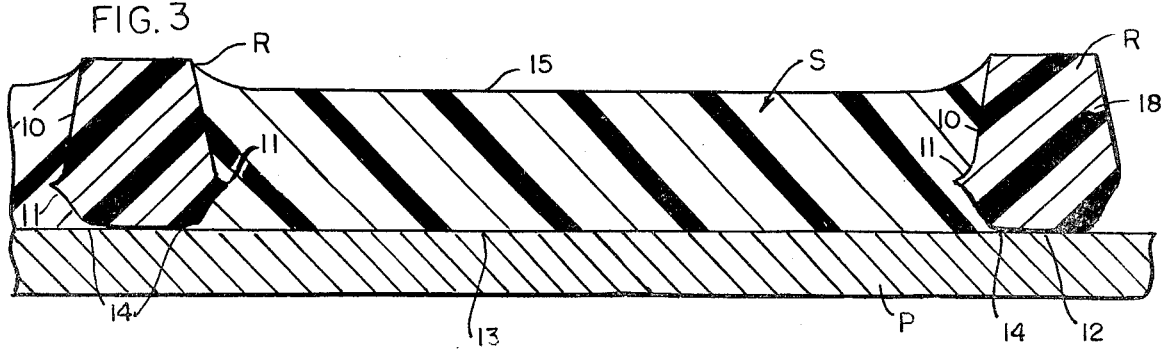

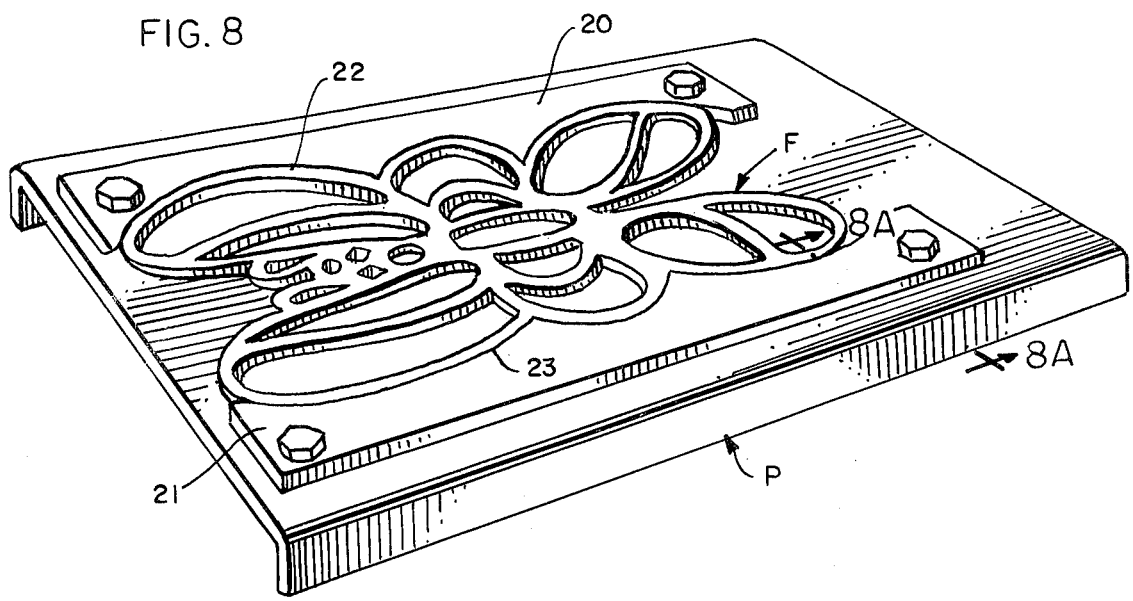
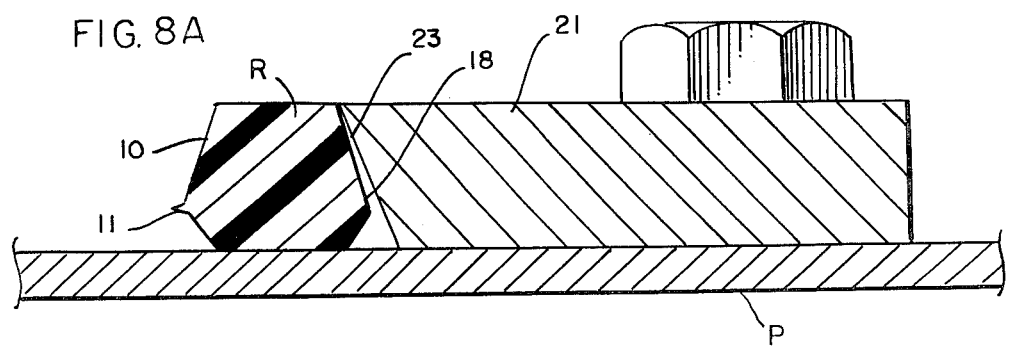
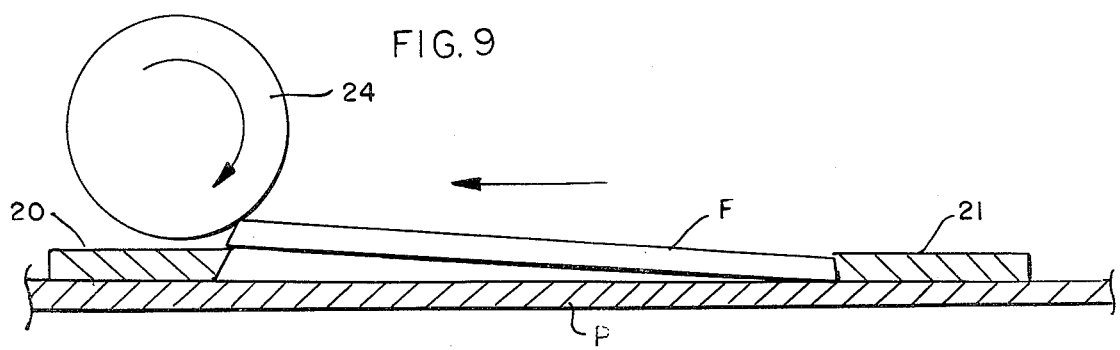

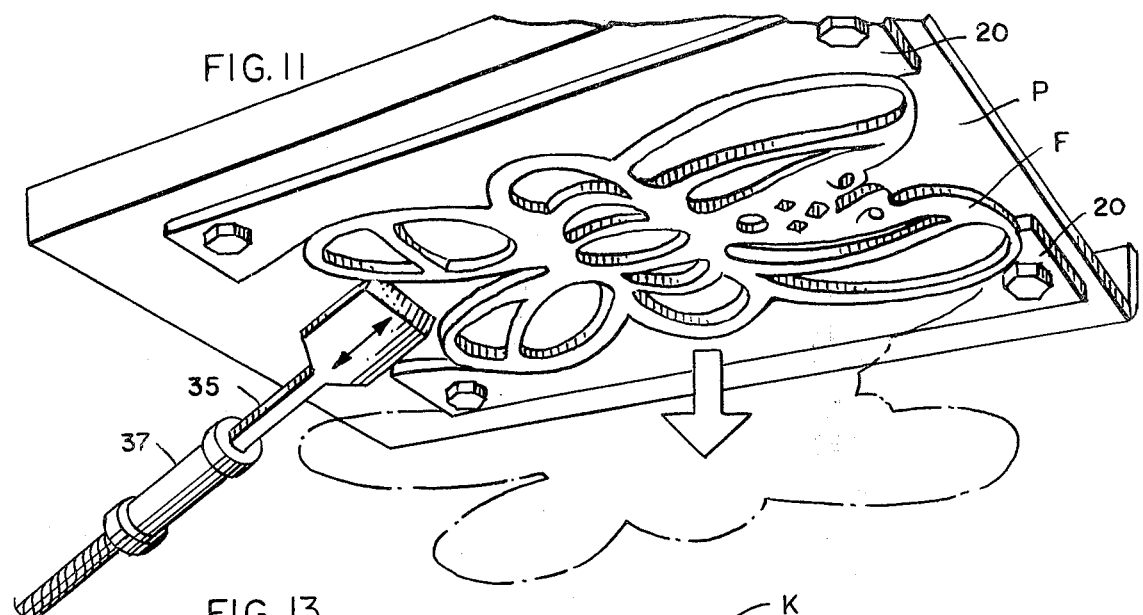
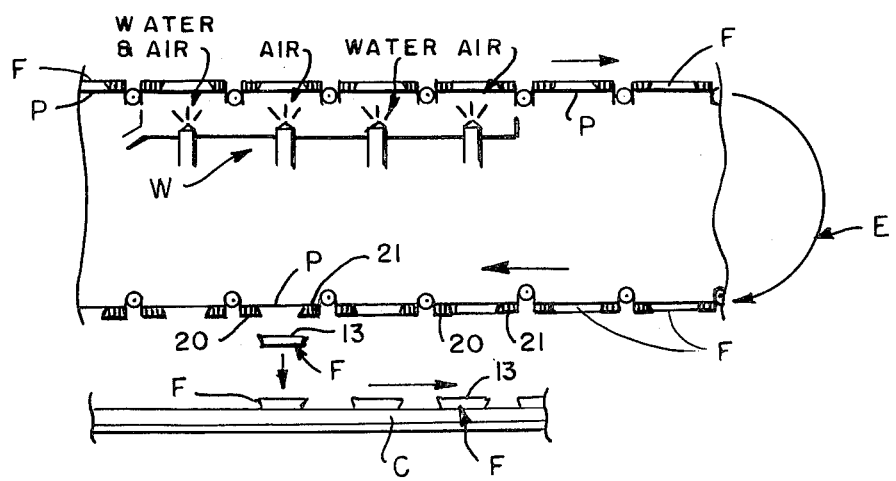
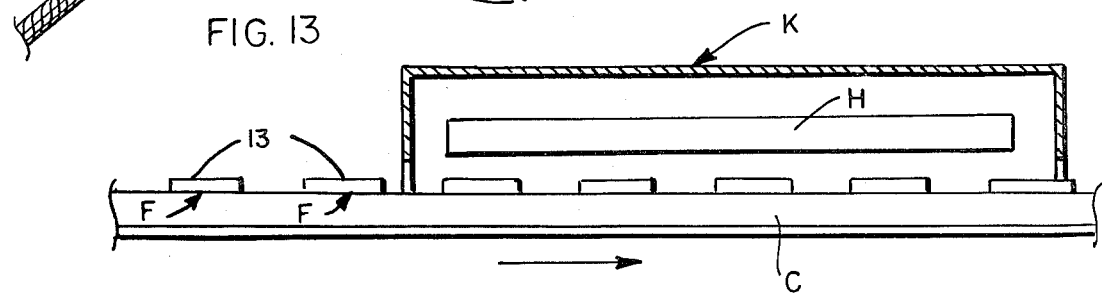

METHOD FOR MAKING PERFUME-RELEASE PLASTIC DECORATIONS

BACKGROUND AND PRIOR ART

The general field of this invention relates to thermoplastic compositions containing a volatile component for release into the atmosphere. Such compositions are known, and are described in U.S. Pat. Nos. 3,725,311, 3,926,655, 4,051,159, 4,095,031, and 4,184,099. As disclosed in the cited patents, the volatile component may be an odor-neutralizing substance or, more commonly, a volatile perfume oil. The thermoplastic resins disclosed for this purpose include a terpolymer of vinyl chloride, vinyl acetate, and vinyl alcohol, which may be used in admixture with a copolymer of vinyl chloride and vinyl acetate, plasticized or unplasticized polyamide resins, copolymers of vinyl acetate and ethyl acrylate, etc. The prior art also discloses that such volatile component-releasing thermoplastic compositions may be formed in various shapes such as by molding or extruding. The cited United States Patents do not specifically describe the insertion of such thermoplastic compositions in frames defining the shape and providing support for the formed resins. However, in the published South African Specification No. 770,610, a stained glass mobile is described which is formed from a metal frame and a hydrophilic thermosetting resin composition containing a perfume oil (see Example IX). In general, the prior art has failed to disclose a satisfactory manufacturing procedure for such products.

In manufacturing perfume-release plastic decorations which resemble stained glass miniatures it is important that the products have an attractive appearance as initially manufactured and that this attractive appearance is maintained during the normal period of use. One problem associated with the manufacture of products having these characteristics is that the perfume component, the volatile perfume oil, must form a substantial part of the composition for effective immediate and sustained release. For example, the compositions may contain from 5 to 25% by weight, or more, of the perfume oil. As the perfume oil evaporates, the compositions tend to shrink or distort. Such shrinkage tends to cause the compositions to separate from enclosing frames. Over the normal period of use of the decorations, which may extend for a number of weeks, the sections of resin composition which are initially secured within the openings of a frame can separate entirely and fall out of the frame. Even before this occurs, however, the partial separation of the resin section from the frame can seriously detract from the appearance of the product.

Another problem relating to the manufacture of products of the character described is that the resin compositions are most attractive when they are prepared in various clear colors. However, it is difficult to manufacture the products with the desired degree of transparency and clarity. In particular, where the resin compositions are heated to a flowable condition for filling the openings of the frame, the bottom surface tends to reproduce the slight irregularities of the supporting surface on which the product is being manufactured, such as, for example, the surface of a Teflon-coated steel plate. When such products are suspended in front of a light source, such as a window, the resin sections may appear clouded or marred.

SUMMARY OF INVENTION

By utilizing the manufacturing method of the present invention, the above-described problems are substantially overcome, and perfume-release plastic decorations can be obtained which have a highly attractive appearance which is maintained during the normal period of use in which the volatile perfume component is released. The segments of the resin compositions within the openings of the enclosing frames are securely integrated to the frames. This provides good mechanical strength and permits some shrinkage of the resin composition to occur during the volatilization of the perfume while retaining separation of the resin sections from the frame. Further, because of the final preferred step in the manufacturing procedure, both surfaces of the resin sections are unmarred and clear. Thus, multiple color resin sections of great clarity can be provided to further enhance the simulation of a miniature stained glass decoration. The steps of a method by which these results are accomplished are described in detail in the following specification.

THE DRAWINGS

The method of this invention and the products produced thereby are shown in preferred and illustrative embodiments in the accompanying drawings, in which FIG. 1 is a perspective view of a frame resembling a butterfly which can be used in practicing the present invention;

FIG. 1A is an enlarged detail perspective sectional view taken on line 1A—1A of FIG. 1 showing the configuration of the ribs of the frame;

FIG. 2 is an elevational view of the frame of FIG. 1 after the openings therein have been filled with the thermoplastic resin compositions by the method of this invention.

FIG. 3 is an enlarged detail sectional view taken on line 3—3 of FIG. 2 showing a filled section of the frame between rib members with the bottom side of the frame resting on a support plate;

FIG. 8 is a perspective view of a support plate and frame holding fixture assembly for use in supporting the frame during filling of the openings with transparent thermoplastic compositions in a variety of colors;

FIG. 8A is an enlarged detail sectional elevational view taken on line 8A—8A of FIG. 8 showing the engagement of one of the holding fixtures with the outside of the frame;

FIG. 9 is a diagramatic elevational view illustrating how the frame may be inserted in the holding fixture of FIG. 8;

FIG. 11 is a diagramatic elevational view illustrating how the frames may be removed from the support plate which are hingedly linked together in the form of a continuous conveyor, after filling and cooling of the frames;

FIG. 12 is diagrammatic view of the support plate conveyor system illustrating the cooling of the plates and the plates thereon after filling of the frames, and the release of the filled and cooled frames from the underside of the plate conveyor;

FIG. 13 is a diagrammatic view illustrating a conveyor and heat tunnel system for clarifying the marred bottom surfaces of the filled and cooled frames;

DETAILED DESCRIPTION

Figure 4:
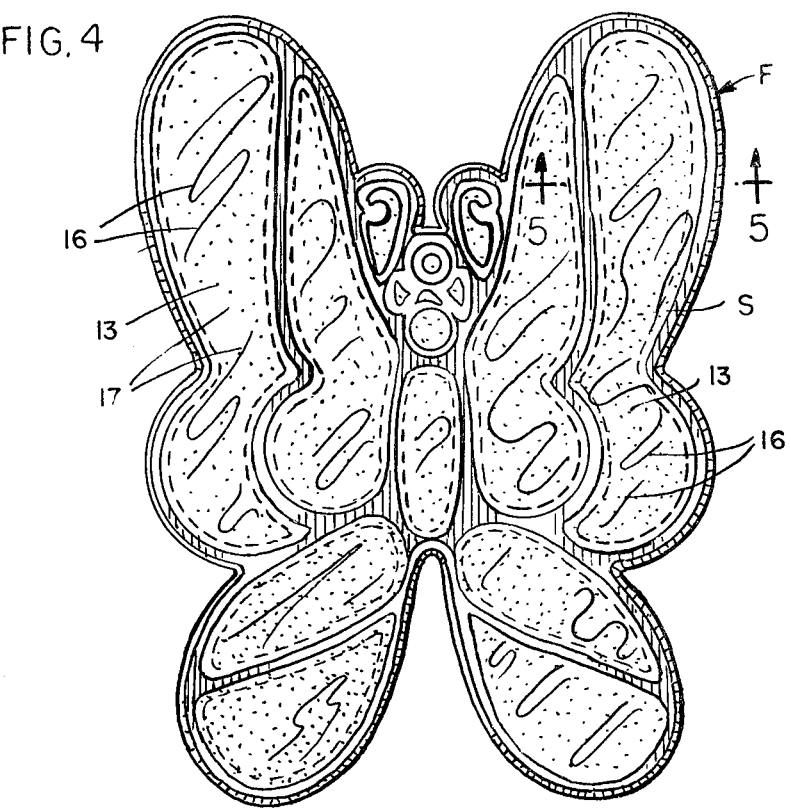
FIG. 4 is an elevational view of the butterfly decoration after completion of the heat integration and solidification of the resin inserts, the butterfly decoration being shown from the side which formed the bottom of the decoration as it was being integrated.
Figure 5:
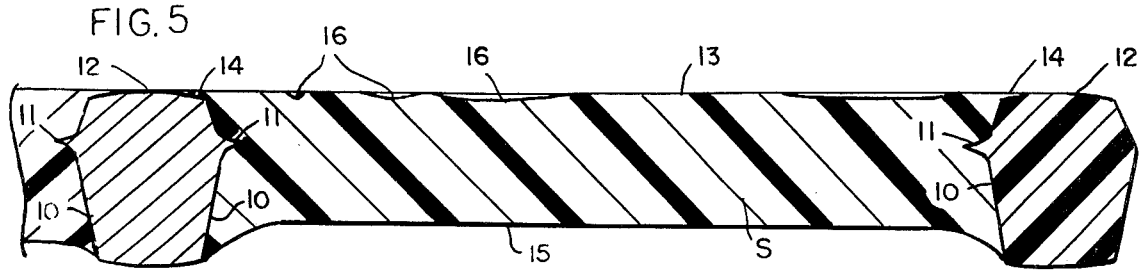
FIG. 5 is an enlarged detail sectional view taken on line 5—5 of FIG. 4.

The manufacturing method of this invention for producing perfume-release plastic decorations comprises a series of steps of filling the openings in the frame with a thermoplastic composition and integrating the filled segments of the composition to the frame. In a typical embodiment a flat shallow frame is held against a horizontally-disposed plate. The frame provides at least one and preferably a plurality of openings therethrough enclosed on its sides by ribs of the frame. The frame holding arrangement is such that the bottom sides of the frame ribs are in smooth contacting engagement with the upper surface of the plate. At least part and preferably all of the frame openings are filled with predetermined quantities of one or more thermoplastic compositions which are flowable with the application of heat at a temperature at which the frame remains rigid. At least one and preferably a plurality of the compositions are colored and light transmitting, that is, transparent or at least translucent. Compositions providing transparent clarity are the most desirable. At least one and preferably a plurality of the compositions will contain a volatile perfume such as a natural or synthetic perfume oil which is slowly released at ordinary room temperatures from its composition after solidification thereof. The filled quantities of the compositions which are to provide the segments for filling the frame openings are caused by the application of heat to flow and to spread outwardly into conforming engagement with the enclosing frame ribs. The filled frame is then cooled to solidify the spread composition quantities, that is, the thermoplastic resin segments, and thereby interlocking the solidified outer edge portions of the thermoplastic resin segments to the frame ribs. The filled frame is then released and removed from the plate.

In an optional but preferred further step, the surface of the filled frame which was in contact with the plate is subjected to a heat treatment to smooth and clarify the surface. For example, the bottom surface of the filled frame as removed from the plate will bear an imprint of any surface irregularities of the plate, and these transferred irregularities will mar the light-transmitting appearance of the colored filled quantities. If so, as a further step in the method, the bottom marred surface is subjected to surface heating to smooth and improve its appearance. The amount of heating should be limited to the melting of a very thin surface layer so that the smoothing and clarifying is achieved without appreciably weakening the security of the interlocking between the frame ribs and the outer portions of the filled resin segments.

Referring now to the drawings to provide more specific illustrations of the foregoing method steps, a frame F in the general form of a butterfly provides multiple openings O therethrough which are surrounded and enclosed by the ribs. The openings O may be of varying size and configuration. Such a frame F is shown in perspective in FIG. 1. Preferably, as shown in FIG. 1A the ribs R have side walls 10 for engaging the edge portions of the resin segments which are preferably of generally convex configuration. The solidified outer edge portions of the resin segments S, as shown in FIGS. 2 and 3, will then enclose the rib sides 10 with a correspondingly convex configuration, as shown more clearly in FIG. 3. Also, it is preferred to provide the intermediate portions of rib walls 10 with projecting fins 11, as shown in FIGS. 1A and 3. The ribs 11 embed themselves in the solidified outer edge portions of the resin segments to assist the security of the interlocking, as shown in FIG. 3.

In a preferred filling procedure, the perfume-containing thermoplastic compositions are filled into the frame openings in molten condition. More specifically, measured increments of the compositions will be injected into the frame openings in the form of a flowable hot melt. As will be subsequently described in greater detail, commercially available hot melt glue applicators can be adapted for this use, such as the "DYNAMELT" portable hot melt dispenser apparatus of LTI Corporation, Monterey, Calif. Such equipment includes pails to hold the resin compositions, a melting platen, heated dispensing hoses and nozzles for applying metered amounts of the hot melt compositions.

During filling of the frame openings, as will also subsequently be described in greater detail, the frame F is secured to a horizontally-extending support plate P. Dispensing nozzles are supported at selected locations above the frame openings, and are connected by hoses to hot melt apparatus of the kind described above. By moving the plate, the same nozzles can be used for injecting the hot melt composition in a plurality of openings of the same frame. Preferably, to assure that the hot melt spreads evenly, heat is applied to plate from the underside. This can be accomplished by using electric radiant heaters beneath the support plate which is formed of a heat conductive metal such as aluminum or steel. It will usually not be necessary also to apply heat from above the frame, since the thermoplastic hot melt composition itself can carry sufficient heat to remain flowable until it is integrated with the frame ribs providing the plate is heated (or preheated) from below to prevent solidification of the portions of the hot melt in contact with the upper surface thereof. After the frames have been filled with the thermoplastic compositions, setting of the liquified compositions is preferably promoted by cooling of the filled frames, and/or the plates on which they are supported. For example, cooling air may be blown over the frames, or the plates may be cooled from the underside by indirect heat exchange with a cooling fluid, such as cold water.

Even though the bottom surfaces 12 of the ribs are held against and smoothly engage the top surface of the support plate P, the outwardly spreading resin composition can flow or creep by capillary action under the bottom sides of the ribs at least part of the way thereacross. As illustrated in FIG. 3, the bottom surface 13 of the spread resin segment S is in contact with the upper surface of plate P which in turn engages the bottom sides 12 of the ribs. The extensions of the resin composition over the rib bottoms 12 is indicated at 14. The extensions 14 will usually not completely cover the bottom surfaces of the ribs. Further, if the bottom sides 12 form a sealing line or area where the resin extension 14 meet from segments of different colors, they will not intermix to an objectionable extent. At the same time, however, the extensions 14 onto the sides 12 will provide a more secure attachment of the segments S to the ribs R.

The surfaces of the plates P in contact with the bottom of the frames F are preferably provided with a coating or with a removable foil which functions as a release surface. The resin mixtures used for filling the frame openings, such as compositions formed from fatty polyamide resins, may be highly adhesive if applied directly to a metal surface, such as aluminum or steel forming the plates. For example, the plates may be coated with Teflon or Mylar sheets may be adhesively attached to the metal surfaces of the plates. In a particularly desirable construction, thin sheets of a release material are removably attached to the plates. For example, Teflon impregnated fiberglass sheets can be used. Such sheet material in the form of tape rolls are available from manufacturers in the United States, such as Taconic Plastics, Inc., Petersburg, N.Y., and Dodge Fluorglass Division, Oak Materials Group, Inc., Hoosic Falls, N.Y. The pressure-sensitive adhesive on such tapes should be selected to be resistant to temperatures up to the highest temperatures encountered in the process, viz. up to about 500° F. Such sheet material can be removed and replaced as required to recondition the plates for further use in the process.

Figure 6:
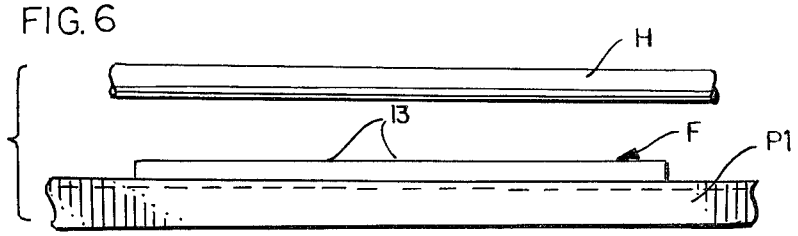
FIG. 6 is a fragmentary diagramatic elevational view of a preferred final step in the manufacturing procedure whereby the marred surface (the bottom surface when forming) of the decoration is smoothed and clarified by surface heating.
Figure 7:
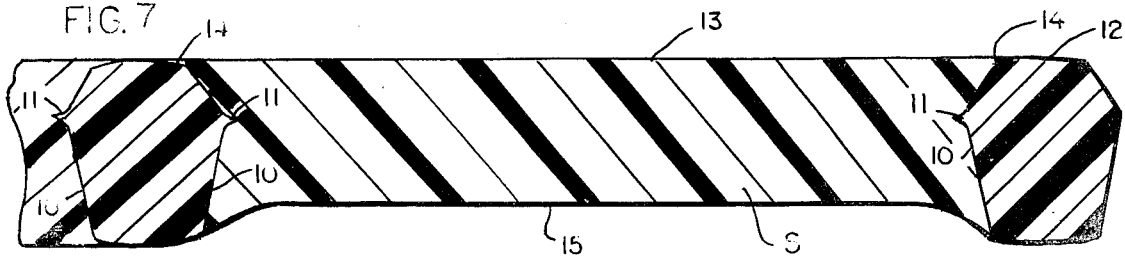
FIG. 7 is an enlarged detail sectional view similar to FIG. 5 showing the smoothed appearance of the bottom surface of the decoration after the heat treatment of FIG. 6.

Usually, however, the upper surface of the support plate will not be perfectly smooth but instead will have minute surface irregularities. These surface irregularities will be transferred to the lower surfaces 13 of the resin segments. The resin segments after cooling and solidification will thereby appear to have surface irregularities which may appear as dots or lines as indicated at 16 and 17 in FIG. 4, being the bottom sides 13 of the segments which were in contact with the plate P. These surface irregularities can be removed by application of radiant heat to the surfaces 13. For example, the filled frame may be inverted with the segment sides 13 uppermost and placed on a support plate P1 as shown in FIG. 6. The radiant heating may then be applied by an electric resistance heater H. This heating is limited in duration and amount so as to produce only a surface heating. Substantially instantaneous liquifraction of a thin surface layer can be obtained, which will remove the surface irregularities (viz. 16, 17). A surface heating procedure of this general character is described in U.S. Pat. No. 4,067,942 for improving the clarity for a specific extruded transparent resin. The smoothed and clarified surface 13 is indicated in FIG. 7. The appearance and light transparency of the resin segments S is thereby improved.

Alternative Filling Procedure

In an alternative for filling the frame openings with the frame supported on a horizontally-extending plate, the resin compositions are prepared in thin sheets which are die-cut to provide the segments for insertion in the frame openings. Such segments may be in the form of solidified wafers, irregular chips, pellets and the like. If desired the wafers can be shaped to drop freely into their corresponding frame openings with their peripheries conforming to the configurations of the enclosing ribs and proximate thereto. The inserted segments will provide a predetermined quantity of the thermoplastic composition for filling the opening into which it is inserted. Sufficient heat can then be applied to the inserted segments to cause them to soften and flow, the required temperature being in the thermoplastic temperature-range of the composition. For example, heat may be applied directly to the segments from above by electric radiant heaters, and also indirectly from beneath through the heat conductive support plate by means of similar heaters. When a temperature is reached at which the plastic segments are flowable, the resin composition of the segments will spread outwardly into conforming engagement with the enclosed ribs in a manner similar to that previously described for hot melt injection filling. The rest of the steps of the method will be essentially the same.

The Resin Compositions

The resin compositions for use in practicing the present invention will contain a suitable thermoplastic resin as the major component and a volatile perfume, such as a natural or synthetic perfume oil, as the other important but lesser quantity component. To reduce the viscosity of the resin compositions when melted and to improve their ease of spreadability, a plasticizer or viscosity reducer can be incorporated. In addition, it is preferred to incorporate a small amount of dye to provide the transparent resin with an attractive color. A general formula for such a composition is set out below.

| Ingredients | Parts by wt. |
| --- | --- |
| Thermoplastic resin | 50-95 |
| Perfume oil | 5-35 |
| Plasticizer | 0-20 |
| Color | 0-1 |

A single thermoplastic resin or mixture of different thermoplastic resins can be employed. In general, the resin or resin mixture is selected to provide thermoplasticity at the desired filling temperature, transparent clarity when solidified, and the ability to gradually release the volatile perfume oil. Thermoplastic compositions which have been used in the prior art for the same or similar purposes can be employed, such as those described in U.S. Pat. Nos. 3,725,311, 3,926,655, 4,051,159, 4,095,031, and 4,184,099. As will be apparent, therefore, a wide variety of such transparent, perfume releasing thermoplastic resins can be used. In preferred, embodiments, however, it is been found that a fatty polyamide resin or mixture of fatty polyamide resins are especially desirable. Such resins are prepared by reaction of polymerized unsaturated fatty acids with polyamines. For example, suitable fatty polyamide resins are prepared by reaction of dimerized linoleic acid with ethylene diamine to obtain polymers of average molecular weights from 6,000 to 18,000.

In the desired formulations, the resin compositions will be composed primarily of such fatty polyamide resins together with a substantial amount, such as at least 5% (by weight) up to 25% or more of the volatile perfume oil. A representative preferred formula of this type is set out below.

| Ingredients | Parts by wt. |
| --- | --- |
| Fatty acid polyamide resin | 60-90 |
| Perfume oil | 10-20 |
| Plasticizer | 5-15 |
| Color | 0-0.2 |

For example, a mixture of fatty acid polyamide resins of different average molecular weight can be used together with a mixture of plasticizers or viscosity reducers, such as nonylphenoxypolyethoxy ethanol and 2-hexyldecanol. The relative proportions of these ingredients may be as set out in the specific formula on the following page.

| Ingredients | Parts by wt. |
| --- | --- |
| (1) Fatty acid polyamide resin (Mol. wt. 10,000-12,000) | 45-55 |
| (2) Fatty acid polyamide resin (Mol. wt. 14,000-18,000) | 20-30 |
| (3) Perfume oil | 10-20 |
| (4) Nonylphenoxypolyethoxy ethanol | 5-12 |
| (5) 2-hexyldecanol | 0.5-2.0 |
| (6) Color | Negligible wt. |

The fatty acid polyamide resins referred to above can be prepared by reacting dimerized linoleic acid with ethylene diamine. Such resins are available commercially from Henkel Corporation, Minneapolis, Minn., as Versamide, Macromelt Cosmedia, and TPX resins, and from other companies in the United States which sell fatty acid polyamide resins.

Material for the frames is not critical. The frames can be formed of any material which retains its rigidity and structured integrity during the heat treatments used in manufacturing the decorations. For example, the frames may be formed of metal or temperature-resistant plastic, such as thermosetting resins or thermoplastics having softening temperatures appreciably above the thermoplastic temperatures of the resin compositions. The latter type of material is particularly desirable since its use will facilitate the molding of the frames with the ribs in the desired configuration, as previously described. For example, the frames may be formed of polyethylene terephthalate which may be reinforced, such as with glass fibers. A commercial material of this kind is sold under the name "Rynite" by E. I. duPont. Processing temperatures up to 400° F. or higher can be used with Rynite frames.

Description of Preferred Apparatus for Practicing Method

In FIG. 8 there is illustrated an advantageous frame holding fixture assembly. It consists of two hold-down fixtures 20 and 21 which are adjustably positioned on and releasably attached to plate P. The fixtures 20, 21 are provided with inner edges 22, 23 which conform exactly to the shape of the outer longitudinally-extending sides of the butterfly frame F. As shown more clearly in FIG. 8A, the outer frame surface 18 inclines outwardly and downwardly, and the corresponding surface 23 of the hold-down fixture also extends outwardly and downwardly. The inclination of both of these surfaces may be identical, or, as shown, the inclination of the fixture surface 23 with respect to the horizontal may be slightly greater, such as about 0.5° to 1° greater. With this design, the frame F can be snapped into the fixture assembly and held securely therein against the upper surface of the plate P. For example, as shown in FIG. 9, the side of the frame F away from the direction of advance of the plate P along a conveyor may be manually inserted against the fixture 21. A pressor roller 24 may be provided to engage the forward end of the frame F as it moves under the roller, causing it to snap into retain position between the fixtures 20, 21, as illustrated in FIG. 8.

After the insertion of the frames in the holding fixture assembly 20, 21, and prior to filling the frames with the thermoplastic composition, it has been found desirable to pre-heat the plates P and the frames F. This can be done by providing electric radiant heaters within the conveyor system arranged to radiate heat onto the underside of the heat conductive metal plates P. For example, the plates may be preheated to a temperature of around 300° F. This will prevent rapid cooling of the thermoplastic composition when it is injected in the openings of the frames. A further advantage is that the pre-heating relaxes any stress within the frames F, permitting their lower surfaces to conform even more closely to the upper surfaces of the support plates. The radiant heating of the plates from the underside may be continued during the injection of the thermoplastic composition. Suitable radiant heaters are the "Chromalox" heaters, supplied by the Edwin L. Wiegand Division of Emerson Electric Company, Pittsburgh, Pa.

Figure 10:
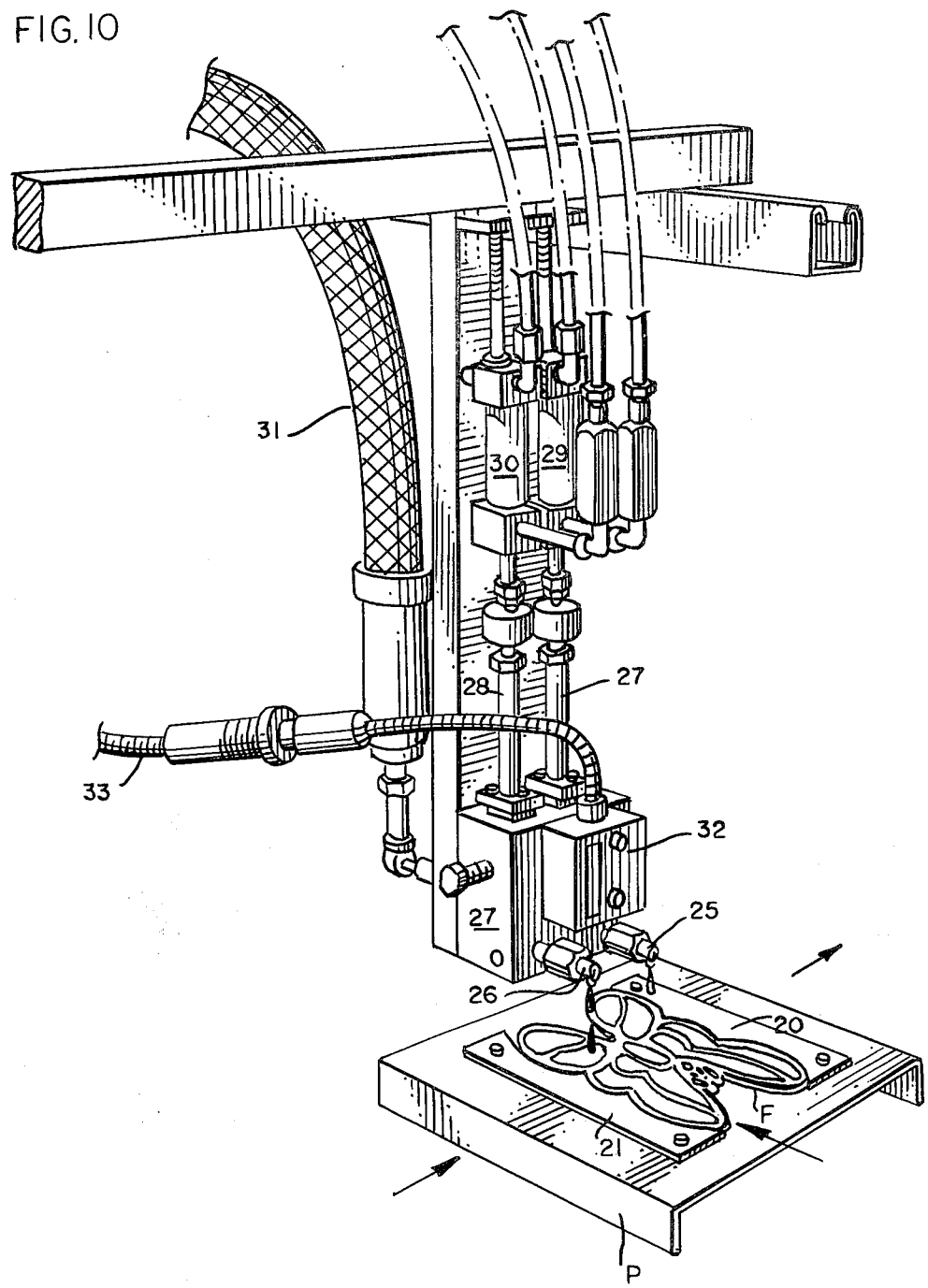
FIG. 10 is a perspective view of a hot melt injection apparatus which may be used with the holding fixture of FIG. 8.

The filling operation is illustrated in FIG. 10. As shown, one of the support plates P, which forms part of the endless conveyor, has moved into position for injection of the thermoplastic composition as a hot melt into two of the openings of the frame. These openings will receive the same composition, which may be a perfume-containing composition of the same color. The dispensing head and nozzle assembly which is supported above the plate P includes dispensing nozzles 25 and 26, which are in fluid communication with two separate measuring chambers within the chamber-providing block 27. Each of these chambers is provided with both inlet and outlet check valves. Positive displacement pistons are provided for reciprocation within the chambers, and are actuated, respectively, by piston rods 27 and 28, which in turn are controlled by air pressure actuated cylinders 29 and 30. The thermoplastic composition in liquid form is supplied through a jacketed and heated hose 31 which at its lower end communicates with the inlet check valves to the dispensing cylinders. To assure that the thermoplastic composition remains in a fluid easily dispensible condition within the cylinders, an electric resistance heater 32 is attached to the cylinder block 27 and provided with an electric connection line 33.

It will be understood that a plurality of sequentially arranged dispensing head and nozzle assemblies, such as the one illustrated in FIG. 10, will be provided for filling all of the openings of the frames. In this way, frame openings may be filled with compositions of different colors, and not all of the filled sections must be compositions containing volatile perfume. With the equipment described, the apparatus can be easily changed-over to operate with a frame F of a different configuration. The hold-down fixtures 20, 21 will be replaced and repositioned as required, and the dispensing units will be repositioned in relation to the openings of the different frame.

With further reference to the dispensing head and nozzle assembly illustrated in FIG. 10, it should be understood that the supply hose 31 will be connected to a "DYNAMELT" hot melt unloader apparatus of LTI Corporation, Monterey, Calif. This apparatus includes closed pails to hold the resin compositions, a melting platen and associated components for transferring the prepared resin compositions in liquified condition to hose 31. This supply system is completely closed, which avoids loss of perfume on liquififaction of the thermoplastic resin mix, after it has been prepared and stored in solidified condition.

After the openings in the frame have been completely filled and the liquid compositions have spread into contact with the frame ribs, it is desirable to cool the filled frames as rapidly as possible to prevent loss of the volatile perfume.

Where the support plates P are connected together in the form of an endless conveyor, as illustrated in FIG. 12, the trays can be moved to a cooling station W after the filling operation. Along the cooling section of the conveyor, cooling fluid may be sprayed onto the underside of the plates, as illustrated in FIG. 12. For example, a sequence of cooling sprays may be used, as illustrated, including a first water and air spray, a second air spray, a third water spray, and a final air spray. In addition, if desired, cooling air may be directed onto the filled frames from above the plates.

As indicated in FIG. 12, the plates P are hingedly connected so that they form an endless conveyor with a return along the bottom of the conveyor. The filled and cooled frames may remain attached to the plates until an intermediate position on the bottom return of the conveyor. At that point, means may be provided for releasing the frames so that they will fall downwardly on a conveyor with the bottom sides of the frames uppermost. This is illustrated in FIG. 12, where a frame F is shown as having been detached, and is dropping downwardly onto the top of a conveyor C.

In the embodiment illustrated in FIG. 12, the conveyor plates P utilize the holding fixtures 20, 21.

As shown in FIG. 11, a suitable release mechanism for detaching the frame may consist of a blade 35 mounted on the outer end of a movable rod 36, which is actuated by a hydraulic cylinder 37. It will be understood that the illustration of FIG. 11 is diagrammatic, and that the exact mechanical construction and mounting is not intended to be shown. FIG. 11 does however illustrate the simplicity of the method of release from the fixtures 20, 21, whereby the release blade 35 can be actuated to unsnap the frame F and permit it to drop downwardly on a conveyor, such as the conveyor C of FIG. 12.

As previously described, the bottom sides of the filled frames which were in contact with the plates P while the frames are being filled will usually have a clouded or marred appearance, which will detract from the clarity and attractiveness of the perfume-release plastic decorations. With the system illustrated, after the frames have dropped onto the conveyor C with their bottom sides 13 uppermost, the conveyor can move the frames into and through an enclosed heating chamber K, as illustrated in FIG. 13. The heating chamber may include an electric resistance heater H, which will radiate infra-red heat onto the upward most bottom surfaces 13 of the frames. The amount of heat is controlled to melt only a thin surface layer, which provides the desired smoothing and clarifying of the surfaces 13 without interfering with the secure interlock between the resin segments S and frame ribs R, as described with reference to FIGS. 2-7. After passing through the heating chamber K, the clarified surfaces 13 of the frames can be cooled by an appropriate cooling means such as air sprays directed onto these surfaces immediately following the exit from the heating chamber K.

Alternate Arrangement for Holding Frames

Figure 14:
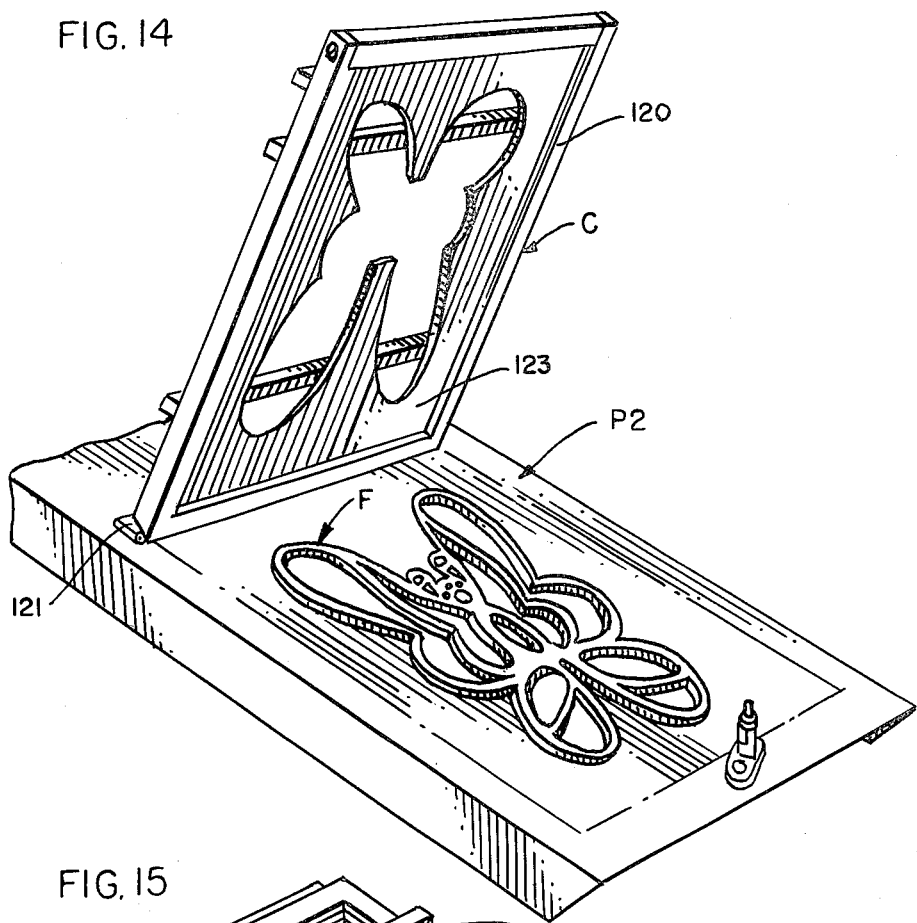
FIG. 14 is a perspective view of a support plate having an alternate frame clamping assembly thereon.

Mechanical arrangements for holding the frames to the support plate during the filling of the frame openings with the resin compositions may be designed to exert clamping pressure distributed along all of the ribs. One such alternate arrangement is illustrated in FIGS. 14 to 17. As shown, the clamp assembly C may be provided with a perimetric frame 120 which has one end hinged at 121 to the top of a plate P2. This permits the clamping assembly to be swung upwardly away from the plate, as shown in FIG. 14. The inner sides of the frame elements 120 may be provided with longitudinally extending slots 122 for slidably receiving a pressor form 123. The end 124 of the clamp assembly opposite the hinged end 121, may be made removable to permit the insertion and removal of differently shaped pressor forms.

Figure 16:
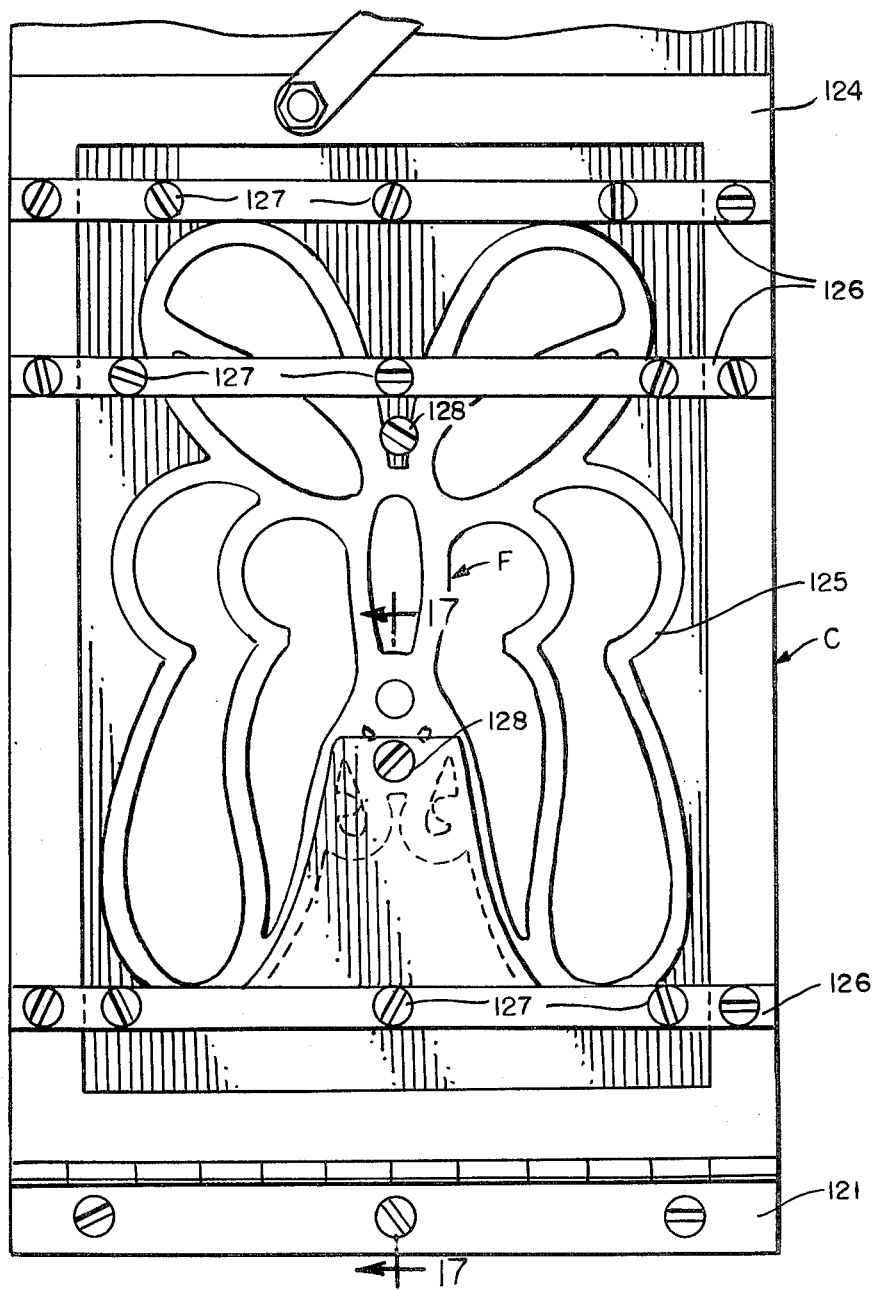
FIG. 16 is a plan view of the clamp assembly of FIGS. 14 and 15.
Figure 17:
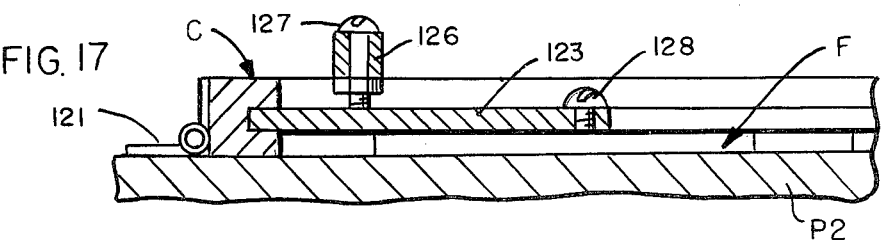
FIG. 17 is a detail sectional view of the alternate clamp assembly taken on line 17—17 of FIG. 14.

In illustration given, form 123 has an opening 125 therein corresponding to the shape of the butterfly form. To provide greater rigidity for the clamping assembly and to facilitate the application of clamping pressure to the form 123, which in turn will be transferred to the frame, a plurality of crossbars 126 can be provided on the top of the clamping assembly. As shown more clearly in FIG. 17, the bars 126 may be attached to the perimetric frame 120 by means of screws so that they can be attached or removed as required. As shown more clearly in FIG. 17, the crossbars 126 may be provided with downwardly extending adjustments screws 127 for bearing against the top of form 123 to exert pressure thereon at selected points, such as those indicated in FIG. 16. In addition, at certain points, such as at the ends of inner extensions, the form 123 may be provided with downwardly extending adjustments screws 128 for exerting controlled pressure against certain of the ribs of the frame. For example, when using the butterfly form, the pressure screws 128 may be provided at two central points, as shown in FIG. 16.

Figure 15:
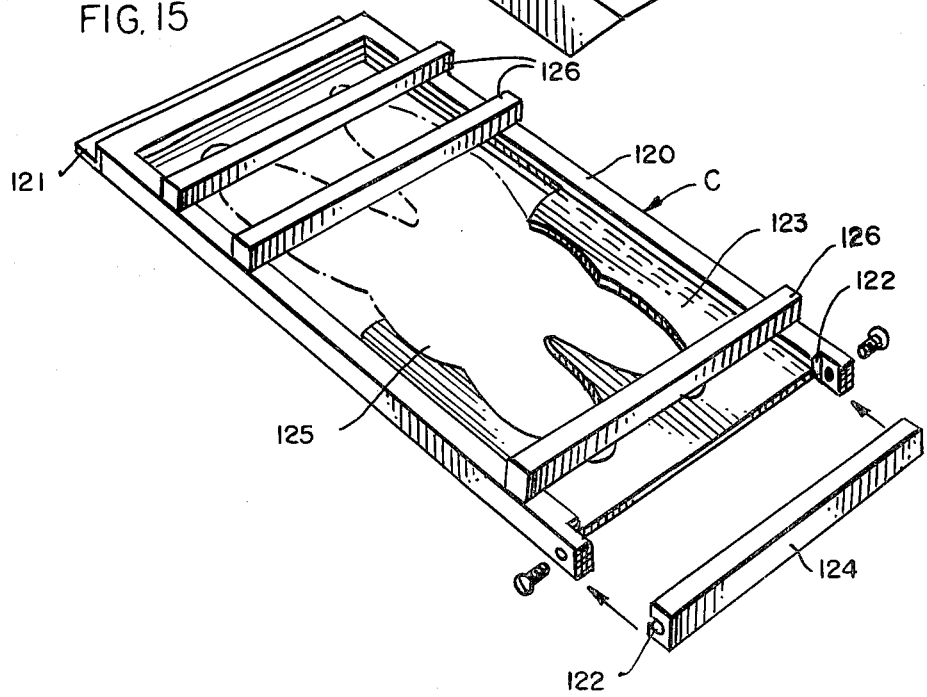
FIG. 15 is an exploded perspective detail view of the clamp assembly of FIG. 14.

As illustrated in FIG. 15, the perimetric frame 120 may be provided with a removable end 124, which on removal permits the pressor form 123 to be slidably removed through the open end of the frame. The pressor forms provided cut-out openings corresponding to frames of different shapes can then be substituted, thereby adapting the clamping assembly for use in holding a wide variety of different shapes of frames in position against the plates P for filling. Similarly, and even more conveniently, the fixtures 20, 21, as previously described, can be removed from the plates P and other holding fixtures substituted which will permit the snap-in insertion of frames of different exterior configuration.

SPECIFIC EXAMPLES

Colored transparent fatty polyamide compositions are prepared for use in practicing the present invention according to the following formulations:

| Scented Red Resin | |
|---|---|
| Ingredients | Wt. % |
| (1) Fatty acid polyamide resin (Henkel TPX 11503, or Cosmedia BC 1283) | 50.2700 |
| (2) Fatty acid polyamide resin (Henkel TPX 11504, or Macromelt 6900) | 25.2000 |
| (3) Perfume oil | 15.5000 |
| (4) Oil Red Dye A-9997 | 0.0300 |
| (5) Nonylphenoxypolyethoxy ethanol | 8.0000 |
| (6) 2-hexyldecanal | 0.0900 |
| | 100.0000 |

| Scented Green Resin | |
|---|---|
| Ingredients | Wt. % |
| (1) Fatty acid polyamide resin (Hendel TPX 11503, or Cosmedia BC 1283) | 50.2700 |
| (2) Fatty acid polyamide resin (Henkel TPX 11504, or Macromelt 6900) | 25.2000 |
| (3) Perfume oil | 15.5000 |
| (4) D & C Green No. 6 | 0.0100 |
| (5) Nitrofast Yellow B | 0.0200 |
| (6) Nonylphenoxypolyethoxy ethanol | 8.0000 |
| (7) 2-hexyldecanal | 1.0000 |
| | 100.0000 |

| Unscented Blue Resin | |
|---|---|
| Ingredients | Wt. % |
| (1) Fatty acid polyamide resin (Hendel TPX 11503, or Cosmedia BC 1283) | 50.2700 |
| (2) Fatty acid polyamide resin (Henkel TPX 11504, or Macromelt 6900) | 25.2000 |
| (3) Nonylphenoxypolyethoxy ethanol | 8.1700 |
| (4) Mineral Oil | 8.1700 |
| (5) 2-hexyldecanal | 8.1700 |
| (6) Nitrofast Blue 2B | 0.0200 |
| | 100.0000 |

In the foregoing formulations, TPX 11503 and Cosmedia BC 1283 are fatty acid polyamide resins believed to have average weights of about 10,000–12,000, softening points of 102–119° C., and viscosities (in poise at 190° C.) of 20.0–55.0. TPX 11504 and Macromelt 6900 are fatty acid polyamide resins usable as hot melt adhesives, which are believed to have average molecular weights of about 14,000–18,000, and softening points of 266–302° F. These fatty acid polyamide resins are available from the Henkel Corporation, Minneapolis, Minn. Nonylphenoxypolyethoxy ethanol is commercially available from Rohm and Haas, Philadelphia, Pa., as Triton N-57, and 2-hexanedecanol is available from the Henkel Corporation, Minneapolis, Minn., as Standamul G-16. As indicated in the formula for the unscented blue resin, the perfume oil may be omitted and mineral oil substituted, where it is not desired to have the perfume oil present in all of the colors of the perfume-release decoration. Other perfume oils and other color dyes can be substituted. The nonylphenoxypolyethoxy ethanol and 2-hexanedecanol are plasticizers for fatty acid polyamide resins. They are included in the formulations primarily to reduce the viscosity of the mixtures when liquified. Other plasticizers or viscosity reducers can be employed, as is well known in the art of formulating polyamide resins.

The formulations may be prepared in sheet form, which are then die-cut to provide the inserts for the frame openings, or they can be formed into a fused pre-mix for hot melt application. In either procedure, it would usually be desirable to first blend ingredients 1 and 2 (the polyamide resin powders), and melt the resin mixture. The melting can be carried out at a temperature in the range of 400° to 475° F. The resin melt can then be heated to about 500° F. and the viscosity reducers added with continual stirring (Triton N-57 and Standamul G-16). With continued mixing and while the temperature is maintained in the range of about 350–360° F., the perfume oil and color dyes are added. Preferably these steps are carried out in a closed container to minimize the loss of the volatile perfume. The completed mixture is then cast or extruded in the form of sheets, or solidified in a cake for use as a hot melt. For application as a hot melt, the solidified mixtures may be remelted using a platen melt temperature of about 350° F. and maintaining temperatures in the hot melt supply hoses from 300° to 350° F.

Multi-opening frames are prepared in various decorative shapes, such as the butterfly configuration illustrated in the drawings, using a thermoplastic resin having a softening point well above the application temperatures to be used for the polyamide resin compositions. The frames may have a thickness in the range of about 1/16 to ⅛ inches, such as for example 3/32 inches. The ribs of the frame may have widths of corresponding size. One suitable commercially available material for manufacturing the frames is sold under the name "Rynite No. 530". This is a fiber-glass filled polyethylene terephthalate resin, which has a softening point of about 650° F. If desired, the frames may be formed from thermosetting resins, or from metals, such as aluminum.

In preparing the completed perfume-release decorations, the method steps described in connection with the drawings can be used. Where the resin composition is formed into a sheet, and inserts cut therefrom, the sheet and inserts can have a thickness corresponding to the thickness of the frame. For example, both the frame and the inserts may have a thickness of 3/32 inches.

We claim:
1. The method of manufacturing a perfume releasing plastic decoration having the appearance of a stained glass miniature comprising:
   (a) positioning a flat shallow frame on the upper surface of a horizontally-disposed plate, said plate being formed of heat conductive metal, said frame providing multiple openings therethrough enclosed on their sides by ribs of said frames and on their bottoms by said plate, said frame being positioned on said plate with the bottom sides of said frame ribs in smooth contacting engagement with the upper surface of said plate;
   (b) applying radiant heat to the underside of said plate for transfer therethrough to preheat the upper surface of said plate and said frame thereon;

(c) while applying heat to said plate filling a plurality of said frame openings with predetermined quantities of one or more flowable thermoplastic compositions containing thermoplastic resin as a principal ingredient, said filled compositions being in contact with the upper surface of said plate, at least one of said compositions being colored and light-transmitting, and at least one of said compositions containing a volatile perfume oil which is capable of being slowly released at ordinary room temperatures from its composition, said perfume-releasing compositions containing from 5 to 35 parts by weight of said volatile perfume oil per each 50 to 95 parts of said thermoplastic resin;

(d) causing said filled quantities of said compositions to spread outwardly on said plate upper surface into conforming engagement with the enclosing frame ribs;

(e) applying a cooling fluid to the underside of said plate to remove heat from said plate and said filled frame thereon to set said compositions within said frame openings in interlocking engagement with said frame ribs; and (f) removing said filled frame from said plate.

2. The method of claim 1 in which a plurality of said plates are connected together to form an endless conveyor, the undersides of said plates being heated and cooled at successive zones within said conveyor.

3. The method of claim 1 in which said predetermined quantities of the thermoplastic compositions are filled in the form of a flowable thermoplastic resin mix maintained at an elevated temperature, and in which all of said compositions are perfume-releasing compositions containing from 10 to 20 parts by weight of said perfume oil per each 60 to 90 parts of said thermoplastic resin.

4. The method of claim 1 in which the bottom surface of said filled frame as removed from said plate bears an imprint of the surface irregularities of said plate which mar the light-transmitting appearance of the colored filled quantities, and in which, as a further step in said method, said bottom surface is subjected to surface heating to smooth said surface and improve said appearance without appreciably weakening the security of said interlocking between said frame ribs and the outer edge portions of said filled quantities.

* * * * *